(12) United States Patent
Straehnz et al.

(10) Patent No.: US 8,777,986 B2
(45) Date of Patent: Jul. 15, 2014

(54) INCISION GUIDE AND WOUND CLOSURE DEVICE AND METHODS THEREFOR

(75) Inventors: Jens-Peter Straehnz, Hamburg (DE); Kerstin Spychaj, Hamburg (DE)

(73) Assignee: Ethicon, Inc., Somerville, NJ (US)

( * ) Notice: Subject to any disclaimer, the term of this patent is extended or adjusted under 35 U.S.C. 154(b) by 321 days.

(21) Appl. No.: 12/774,115

(22) Filed: May 5, 2010

(65) Prior Publication Data
US 2011/0276089 A1    Nov. 10, 2011

(51) Int. Cl.
*A61B 17/03*    (2006.01)
(52) U.S. Cl.
USPC ........................................... 606/217
(58) Field of Classification Search
CPC ................ A61B 17/08; A61B 17/085; A61B 2017/085; A61B 2017/086; A61B 2017/088; A61B 2017/320052
USPC ............ 606/216–217, 213–215; 24/437–441; 602/41, 54
See application file for complete search history.

(56) References Cited

U.S. PATENT DOCUMENTS

| | | | |
|---|---|---|---|
| 1,220,602 A * | 3/1917 | Campbell et al. | 24/437 |
| 3,933,158 A | 1/1976 | Haverstock | |
| 4,038,989 A | 8/1977 | Romero-Sierra et al. | |
| 4,114,624 A | 9/1978 | Haverstock | |
| 4,467,805 A | 8/1984 | Fukuda | |
| 4,535,772 A * | 8/1985 | Sheehan | 606/218 |
| 4,676,245 A | 6/1987 | Fukuda | |
| 4,881,546 A | 11/1989 | Kaessmann | |
| 5,026,389 A | 6/1991 | Thieler | |
| 5,993,804 A * | 11/1999 | Read et al. | 424/93.72 |
| 6,007,564 A | 12/1999 | Haverstock | |
| 6,106,554 A | 8/2000 | Bretton | |
| 7,594,914 B2 | 9/2009 | Luchetti | |
| 2009/0270884 A1 * | 10/2009 | Hake | 606/139 |

FOREIGN PATENT DOCUMENTS

WO    WO 2009/135002 A1    11/2009

OTHER PUBLICATIONS

Roolker et al., "Results of a Prospective Randomised Study Comparing a Non-invasive Surgical Zipper Versus Intracutaneous Sutures for Wound Closure," Arch. Orthop. Trauma Surg., vol. 122, pp. 2-4, 2002.
Bastian et al., "A New Form of Noninvasive Wound Closure With a Surgical Zipper," The Journal of Urology, vol. 169, pp. 1785-1786, May 2003.
Zutt et al., "Medizinischer Reissverschluss-verband bei Wunderverschluss Unter Spannung" (Improved Scar Formation After Using a Medical Surgical Zipper for Wound Closure Under Tension), Hautarzt, vol. 54, pp. 342-347, Mar. 2003.
International Search Report mailed Aug. 22, 2011 for corresponding Patent Application No. PCT/US2011/034990.
U.S. Appl. No. 09/177,227, filed Jul. 9, 2009, Warren.

* cited by examiner

*Primary Examiner* — Julian W Woo
*Assistant Examiner* — Shaun L David

(57) ABSTRACT

An incision guide and wound closure device includes a surgical mesh having a top surface and a bottom surface, and first and second incision guides affixed to the top surface of the surgical mesh. The bottom surface of the mesh is adhered to tissue using clear or translucent adhesive. The first and second incision guides have opposing alignment surfaces that are adapted to guide a cutting instrument for making an incision through the mesh and into the tissue. The device has a closing element that is moveable along the length of the respective first and second incision guides for drawing the first and second alignment surfaces toward one another for closing the incision opening in the tissue.

18 Claims, 11 Drawing Sheets

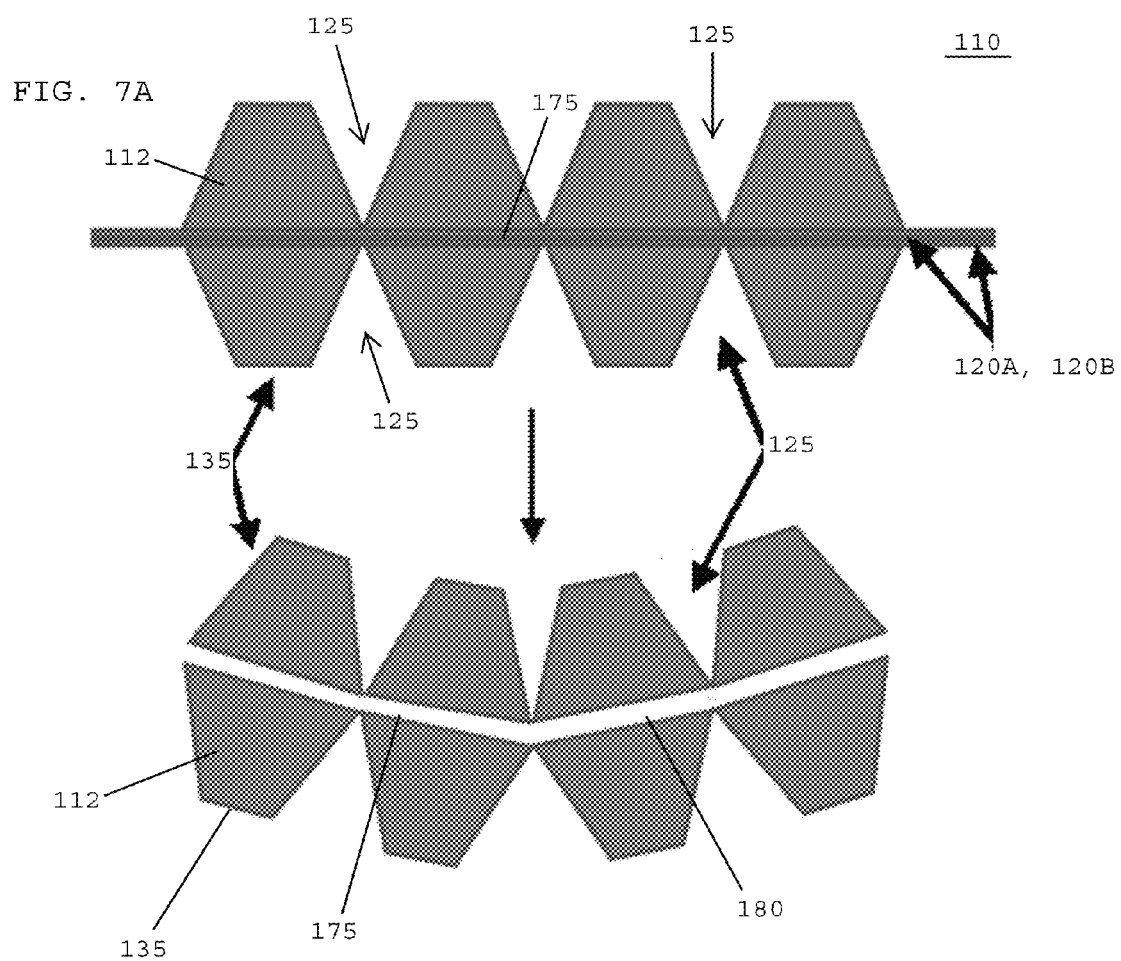

INCISION GUIDE AND WOUND CLOSURE DEVICE AND METHODS THEREFOR

BACKGROUND OF THE INVENTION

1. Field of the Invention

The present application generally relates to surgical instruments, and more specifically relates to incision guides and wound closure devices.

2. Description of the Related Art

During surgical procedures, incisions are often made, and these incisions must be closed at the end of the surgery. Over the years, many different techniques have been developed for closing surgical incisions. One common technique involves using sutures having a single knot or a series of knots. In recent years, surgical tacks have been used for closing surgical incisions, which reduces the amount of time required for closing incisions.

There are a number of disadvantages associated with using sutures for closing surgical incisions including an increased likelihood of wound infection due to a compromise of epidermal blood supply, high amounts of foreign body material, and tension on the wound edges. Using sutures and surgical tacks also typically results in poor aesthetics due to scar formation, stitch/tacker channels, and irritation of the skin.

In order to avoid the aesthetic problems outlined above, many surgeons now use an intradermal suture technique with absorbable or non-absorbable sutures. Unfortunately, this technique is time consuming, and requires non-absorbable sutures to be removed. In addition, even in instances where absorbable sutures are used, there remains a likelihood of granuloma formation.

A different technique for closing wounds or surgical incisions involves using glues such as a Dermabond adhesive. Typically, the Dermabond adhesive is used for small cuts and minor wounds, mainly on the face and head where skin tension is low. In the case of larger wounds, an exact approximation of wound edges is required to reduce the tension that may develop at the wound edges. Therefore, a two-layer closure of subcutis and dermis is required.

There have been a number of advances related to closing wounds without using surgical tacks or sutures. For example, U.S. Pat. No. 7,594,914 to Luchetti discloses an incision and closure device designed to repair skin wounds. The device includes a slide fastener that is fitted to a self-adhesive sheet that is attached to the skin surface. The slide fastener has a slider that includes a contact electrode for electrocoagulation and a cutting edge. As the slide fastener is opened, the slider simultaneously makes an incision by means of the cutting edge, severing both the flexible sheet and the skin beneath. For closing the incision, stringer tapes of the slide fastener interlock by the action of the slider, thereby bringing both the edges of the flexible sheet and the wound closure beneath into apposition. As the slider is drawn forward for closing the stringer tapes, electrical energy is applied by the electrode at the union site of the wound edges, which were previously brought into apposition by the mechanical action of the slide fastener, thus insuring that the edges become adhered in full depth as a result of electrical coagulation.

U.S. Pat. No. 3,933,158 to Haverstock discloses a skin closure means including a device for uniting and holding separable closure members and skin portions attached thereto accurately together for preventing separation. The device includes portions for accurately aligning and holding the separated edges of a skin wound or incision together during healing in such a way as to minimize or prevent the formation of scar tissue. The device includes closures that may be quickly and accurately applied, even under adverse conditions such as during emergencies and war conditions, and also under more controlled conditions such as in operating rooms and doctors' offices. Referring to FIG. 9 of Haverstock, a split tubular member 36 is used to hold opposing portions 28 and 30 together.

In spite of the above advances, there remains a need for an incision guide and wound closure device that reduces the length of surgeries, eliminates stitch channels, reduces tension on wound edges, minimizes or eliminate intracutaneous foreign body material, decreases infection rates, is easy to apply, results in a better cosmetic outcome, eliminates the need to remove stitches or tacks, enables large wounds or incisions to be easily closed, protects the wound by providing a sealing effect, and eliminates the need for additional wound dressing material. There also remains a need for an incision guide and wound closure device that may be repositioned atop a skin surface for ensuring proper alignment over a surgical site, and that provides an at least translucent or clear viewing area for observing the healing wound and the surrounding tissue.

SUMMARY OF THE INVENTION

In one embodiment, an incision guide and wound closure device preferably includes a surgical mesh having a top surface, a bottom surface, and a plurality of pores or openings extending between the top and bottom surfaces. The device desirably includes a first incision guide affixed to the top surface of the surgical mesh, the first incision guide having a first end, a second end, and a first alignment surface extending between the first and second ends thereof. The device preferably includes a second incision guide affixed to the top surface of the surgical mesh adjacent the first incision guide, the second incision guide having a first end, a second end, and a second alignment surface extending between the first and second ends thereof that opposes the first alignment surface of the first incision guide. In one embodiment, the device preferably includes a closing element engageable with the first and second incision guides, the closing element being moveable between the first and second ends of the respective first and second incision guides for drawing the first and second alignment surfaces toward one another so as to close an incision opening.

In one embodiment, the first and second alignment surfaces preferably define an elongated gap between the adjacent incision guides that is preferably adapted to receive a cutting instrument, such as a scalpel, for cutting through the surgical mesh to form an incision through the surgical mesh that extends between the first and second incision guides. The incision preferably extends into tissue for performing a surgical procedure. The first and second alignment surfaces on the adjacent incision guides are preferably adapted to engage the cutting instrument for properly aligning the cutting instrument relative to the top surface of the surgical mesh. In one embodiment, the alignment surfaces maintain the cutting instrument perpendicular to a skin surface so that the incision is not sloped relative to the skin surface. In one embodiment, the incision through the surgical mesh is desirably closed as the closing element moves along the length of the respective first and second incision guides.

In one embodiment, the incision guide and wound closure device preferably includes a first adhesive covering the bottom surface of the surgical mesh for forming a relatively weaker bond between the surgical mesh and a skin surface. The weak bond may be broken by peeling the mesh away from the skin and repositioning the mesh atop a skin surface for properly aligning the mesh. The above action may be repeated until surgical personnel are satisfied that the device is properly positioned and aligned. In one embodiment, a second adhesive may be passable through the plurality of pores of the surgical mesh for forming a relatively stronger bond between the surgical mesh and the skin surface. In one embodiment, the first adhesive is adapted to form a weaker bond between the surgical mesh and the skin surface, and the second adhesive is adapted to form a stronger bond between the surgical mesh and the skin surface. In one embodiment, the second adhesive forms a more permanent bond between the mesh and the tissue/skin that may not be removed for about one week and more preferably about 10-12 days. In one embodiment, the second adhesive is preferably clear or translucent for enabling visibility of the incision and the skin surrounding the incision. As a result, the condition of the incision and the skin around the incision may be monitored for observing healing, infection, etc.

In one embodiment, the first incision guide preferably includes a first base having a bottom surface that is desirably permanently secured to the top surface of the surgical mesh and a first flange projecting upwardly from the first base. In one embodiment, the second incision guide preferably includes a second base having a bottom surface is desirably permanently secured to the top surface of the surgical mesh and a second flange projecting upwardly from the second base.

In one embodiment, the securing element is desirably adapted to move or slide over the first and second flanges for drawing the first and second incision guides toward one another for closing the incision opening. As the incision guides are drawn together, the opposing cut edges of the mesh are drawn together, which, in turn, draws the opposing edges of the wound together due to the fact that the mesh is strongly secured to the underlying skin or tissue. In one embodiment, the first flange has a first outer surface and a first inner surface defining a first elongated channel that extends along a length of the first flange, and the second flange has a second outer surface and a second inner surface defining a second elongated channel that extends along a length of the second flange. In one embodiment, the first and second flanges may be curved so that the inner surfaces define concave surfaces and the outer surfaces define convex surfaces.

In one embodiment, the closing element desirably includes a slideable element adapted to slide over the first and second outer surfaces of the respective first and second flanges, and an elongated core coupled with the slideable element. As the slideable element moves from the first ends to the second ends of the second incision guides, the slideable element is preferably adapted to pull the elongated core through the first and second elongated channels of the first and second flanges. In one embodiment, the elongated core desirably includes a first tubular element adapted to advance within the first elongated channel, a second tubular element adapted to advance within the second elongated channel, and an elongated slat interconnecting the first and second tubular elements.

In one embodiment, the elongated slat preferably has a leading end and an opening adjacent the leading end, and the slideable element includes an attachment flange engageable with the slat opening for connecting the slideable element and the elongated core together. In one embodiment, the first elongated channel desirably has a first linear opening and the first tubular element has a diameter that is larger than the first linear opening so that is may not pass through the first linear opening. As a result, the first tubular element may slide axially within the first elongated channel, but may not pass laterally through the first linear opening. In one embodiment, the second elongated channel preferably has a second linear opening and the second tubular element has a diameter that is larger than the second linear opening. As a result, the second tubular element may slide axially within the second elongated channel, but may not pass laterally through the second linear opening. In one embodiment, the first and second linear openings preferably oppose one another so that the elongated slat is extendable through the first and second linear openings as it interconnects the first and second tubular elements. As the slideable element pulls the elongated core, the elongated slat may move axially through the linear openings while interconnecting the tubular elements.

In one embodiment, the first and second incision guides affixed to the mesh are preferably flexible for forming non-linear incisions. In one embodiment, one or more slits or cuts may be formed in the surgical mesh, such as in a peripheral region of the mesh, for flexing the first and second incision guides to form a non-linear gap between the first and second incision guides. A non-linear incision, such as a curved incision, may be formed between the incision guides. The closing element may be used for drawing the incision guides together and closing the incision.

In one embodiment, an incision guide and wound closure device preferably includes a surgical mesh, and first and second incision guides projecting above a top surface of the surgical mesh. The first and second incision guides are preferably located adjacent one another and have opposing alignment surfaces adapted to guide a cutting instrument for forming an incision through the surgical mesh and into tissue. As the incision is formed, the adjacent incision guides may move away from one another as the incision opening becomes larger. The device preferably includes a closing element engageable with the first and second incision guides. The closing element is preferably moveable along the length of the incision guides for drawing the first and second alignment surfaces toward one another for closing the incision opening previously formed in the surgical mesh.

In one embodiment, the surgical mesh preferably has a plurality of pores extending therethrough, and a clear or translucent adhesive may be passable through the pores for adhering the surgical mesh to a skin surface. The adhesive may be applied in a fluid form and cured.

In one embodiment, a method of making and closing an incision includes providing an incision guide and wound closure device including a mesh having a top surface and a bottom surface, first and second incision guides affixed to the top surface of the mesh, and a closing element engageable with the first and second incision guides. The method preferably includes positioning the bottom surface of the mesh atop tissue, applying an adhesive to the mesh for adhering the mesh to the tissue, and advancing a cutting instrument between the first and second incision guides for making an incision through the mesh and into the tissue. The method may include performing a surgical procedure within the incision, and sliding the closing element along the first and second incision guides for drawing the guides toward one another for closing the incision.

Although the present invention is not limited by any particular theory of operation, it is believed that the incision guide and wound closure device disclosed herein provides a number of benefits over prior art devices. First, the present invention combines a surgical mesh with a slideable closure system. As such, the mesh may be re-positioned if it is not properly aligned atop tissue at a surgical site. This is not possible with conventional systems having a film with an adhesive. In addition, in one embodiment, the closure device disclosed herein is applied prior to making an incision, which ensures exact reapproximation of wound edges after the surgical procedure has been completed. A glue or adhesive may be passed through the pores of the mesh after the mesh is properly positioned atop the skin. In addition, in one embodiment, the present invention provides better fixation on the skin due to the combination of a surgical mesh and glue. In one embodiment, the incision guide and wound closure device disclosed herein ensures the exact positioning and alignment of a cutting tool such as a scalpel, which preferably avoids sloped incisions. In one embodiment, the closing element for closing the device has an enhanced design and function including a plastic core part of the closing element that is more stable, flexible and less bulky compared with previous devices. In one embodiment, a wound healing and/or infection fighting substance may be applied to the surgical mesh for minimizing the likelihood of infections and promoting wound healing.

These and other preferred embodiments of the present invention will be described in more detail below.

BRIEF DESCRIPTION OF THE DRAWING

FIG. 5C-1 shows a magnified view of a section of the incision guide and wound closure device shown in FIG. 5C.

FIG. 5E-1 shows a magnified view of the distal ends of the incision shown in FIG. 5E.

FIGS. 7A-7B show an incision guide and wound closure device, in accordance with one embodiment of the present invention.

DETAILED DESCRIPTION

Figure 1:
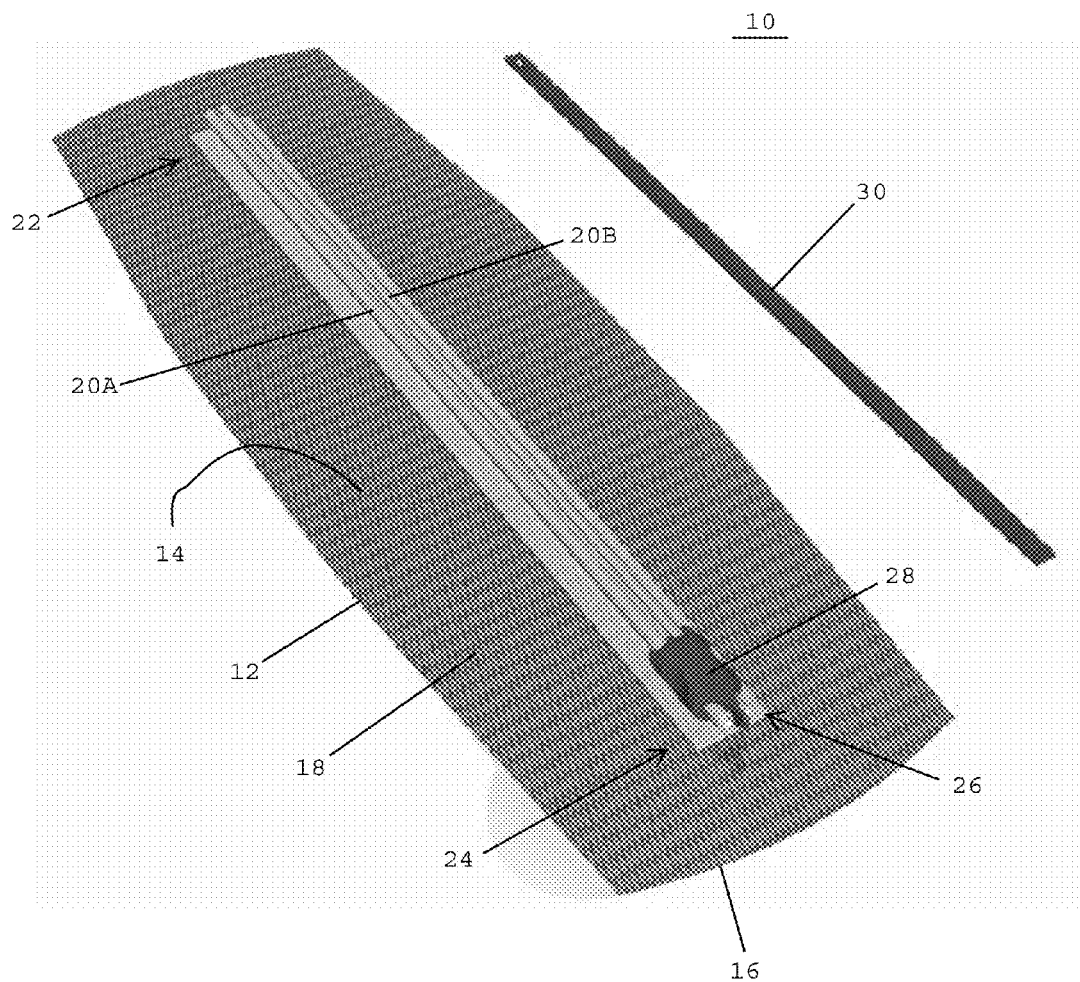
FIG. 1 shows a perspective view of an incision guide and wound closure device including a surgical mesh, incision guides attached to the surgical mesh, and a closing element including a slideable guide and an elongated core, in accordance with one embodiment of the present invention.

Referring to FIG. 1, in one embodiment, an incision guide and wound closure device 10 preferably includes a surgical mesh 12 having a top surface 14, a bottom surface 16, and a plurality of openings or pores 18 extending between the top and bottom surfaces 14, 16. In one embodiment, the plurality of pores 18 extending through the surgical mesh 12 desirably enable medical personnel to have visibility through the mesh for observing an underlying incision and the tissue surrounding the incision. The plurality of openings 18 extending through the surgical mesh 12 also preferably enable an adhesive to be passed through the openings for forming a strong bond between the surgical mesh and the underlying skin. In one embodiment, the openings or pores in the surgical mesh have a diameter of about 1 mm. In one embodiment, the surgical mesh may include a polypropylene mesh. In one embodiment, the surgical mesh may include a substantially flat monofilament polypropylene mesh with reinforcement filaments. The mesh preferably has a width of about 3 cm, however, the exact width may vary in response to surgical needs. The length of the surgical mesh may also vary depending upon surgical needs.

In one embodiment, prior to making an incision, the bottom surface 16 of the surgical mesh 12 may be positioned against the skin surface of a patient. The bottom surface 16 may have a slight or weak adhesive layer applied thereto for forming a non-permanent and/or repositionable frictional engagement with the skin surface. Due to the slight or weak adhesive layer, if an initial positioning of the surgical mesh on a patient's skin is not acceptable (e.g. misaligned), the surgical mesh 12 may be lifted or peeled away from the patient's skin for re-positioning. Once medical personnel are satisfied that the surgical mesh 12 has been properly positioned or aligned atop the skin (e.g. properly aligned with a surgical site where an incision will be made), an adhesive, such as a clear or translucent adhesive may be applied over the top surface 14 of the surgical mesh 12 for passing through the plurality of openings 18 to more permanently and/or more firmly affix the surgical mesh to the skin. In one embodiment, the clear or translucent adhesive preferably includes tissue glue such as Cyanoacrylate.

In one embodiment, the incision guide and wound closure device 10 preferably includes opposing first and second incision guides 20A, 20B that are preferably attached to the top surface 14 of the surgical mesh 12. The incision guides preferably project above the top surface 14 of the surgical mesh 12. As will be described in more detail below, the opposing first and second incision guides 20A, 20B define an elongated incision opening extending therebetween that is preferably used for aligning and guiding a surgical tool, such as a scalpel, for making an incision through the surgical mesh 12 and into the tissue of a patient. In one embodiment, the incision guides 20A, 20B desirably align a cutting tool so that it is substantially perpendicular to the skin surface so as to prevent the formation of an angled or sloped incision in the tissue.

In one embodiment, each incision guide 20A, 20B preferably has a proximal end 22 and a distal end 24 remote therefrom. The incision guide and wound closure device 10 preferably includes a closing element 26 having a slideable guide 28 adapted to move between the second or distal ends 24 and the first or proximal ends 22 of the respective incision guides 20A, 20B, and an elongated core 30 attachable to the slideable guide 26.

As will be described in more detail below, in one embodiment, after an incision is made between the opposing first and second incision guides 20A, 20B, the wound may be closed by sliding the slideable guide 28 and the elongated core 30 form the distal end 24 toward the proximal end 22 of the first and second incision guides 20A, 20B. As the closing element 26 moves toward the proximal end 22, the slideable guide 28 and the elongated core 30 pull the opposing incision guides 20A, 20B together, which, in turn, pull the opposing edges (not shown) of the mesh 12 together. The mesh, in turn, pulls the underlying tissue together for closing the wound.

Figure 2A:
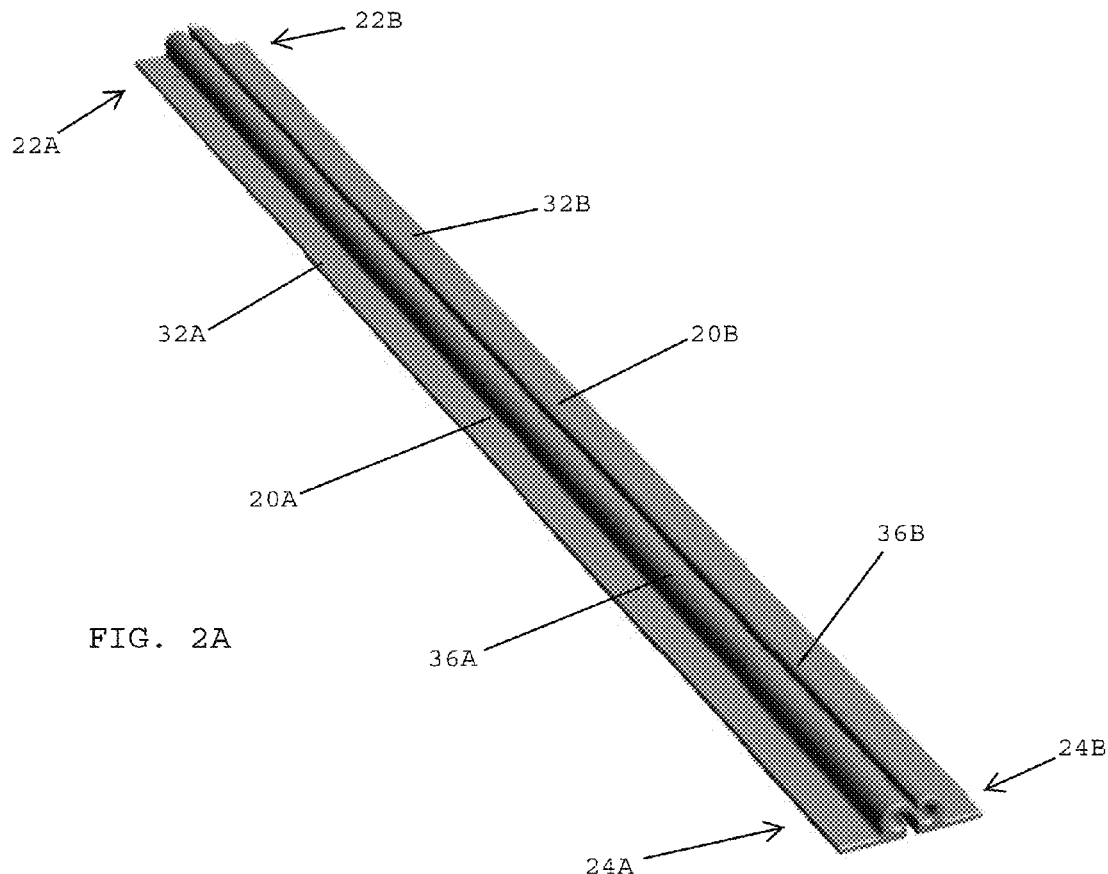
FIG. 2A shows a perspective view of the of incision guides of FIG. 1, in accordance with one embodiment of the present invention.
Figure 2B:
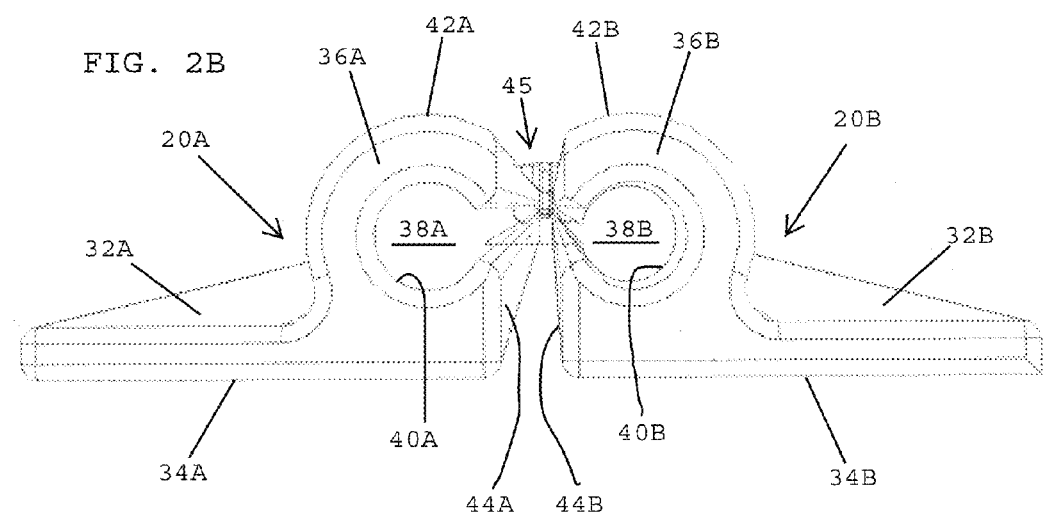
FIG. 2B shows an end view of the incision guides of FIG. 2A.

Referring to FIG. 1, in one embodiment, the opposing first and second incision guides 20A, 20B are preferably secured to the top surface 14 of the surgical mesh 12. Referring to FIGS. 2A and 2B, in one embodiment, the first incision guide 20A preferably includes a base 32A having a substantially flat bottom surface 34A that is attached to the top surface 14 of the surgical mesh 12 (FIG. 1). The first incision guide 20A preferably includes a curved flange 36A defining a first elongated channel 38A extending from the distal end 24A to the proximal end 22A thereof. The first curved flange 36A preferably has a first inner surface 40A that defines the elongated channel 38A and a first outer surface 42A. In one embodiment, the first inner surface may define a concave surface and the first outer surface may include a convex surface. The exact geometric shape of the first inner and outer surfaces 40A, 42A may be modified (e.g. square) and still fall within the scope of the present invention.

In one embodiment, the incision guide and wound closure device 10 preferably includes a second incision guide 20B having a base 32B with a bottom surface 34B adhered to a top surface 14 of the surgical mesh 12 (FIG. 1). The second incision guide 20B preferably includes a second curved flange 36B defining a second elongated channel 38B that extends between the distal end 24B and the proximal end 22B of the second incision guide 20B. The second incision guide 20B preferably includes a second inner surface 40B that defines the second elongated channel 38B, and a second outer surface 42B that defines an outer surface of the second curved flange 36B. In one embodiment, the second inner surface may define a concave surface and the second outer surface may include a convex surface. The exact geometric shape of the second inner and outer surfaces 40B, 42B may be modified (e.g. square) and still fall within the scope of the present invention.

Referring to FIG. 2B, in one embodiment, the opposing first and second incision guides 20A, 20B have opposing incision guide surfaces 44A, 44B that extend upwardly from the top surface 14 of the surgical mesh 12. The opposing incision guide surfaces 44A, 44B preferably align and guide a cutting instrument, such as a scalpel (not shown), as medical personnel make an incision through the surgical mesh 12 (FIG. 1) and into the tissue of a patient. The opposing guide surfaces 44A, 44B preferably define an elongated gap or opening 45 that extends along the length of and between the opposing first and second incision guides 20A, 20B for guiding a surgical instrument. In one embodiment, a surgical mesh 12 (FIG. 1) is preferably positioned atop a patient's skin so that the opposing guide surfaces 44A, 44B are aligned with a desired location for an incision to be formed into the patient's tissue. If medical personnel are not satisfied that the elongated opening 45 between the first and second guides 20A, 20B is properly aligned, the surgical mesh 12 may be lifted away from the skin for repositioning the first and second incision guides over the patient's tissue. Once medical personnel are satisfied that the incision guides 20A, 20B are properly aligned, a clear or translucent tissue glue may be passed between the plurality of pores 18 extending through the surgical mesh 12 for firmly affixing the surgical mesh 12 to the patient's tissue.

Figure 3A:
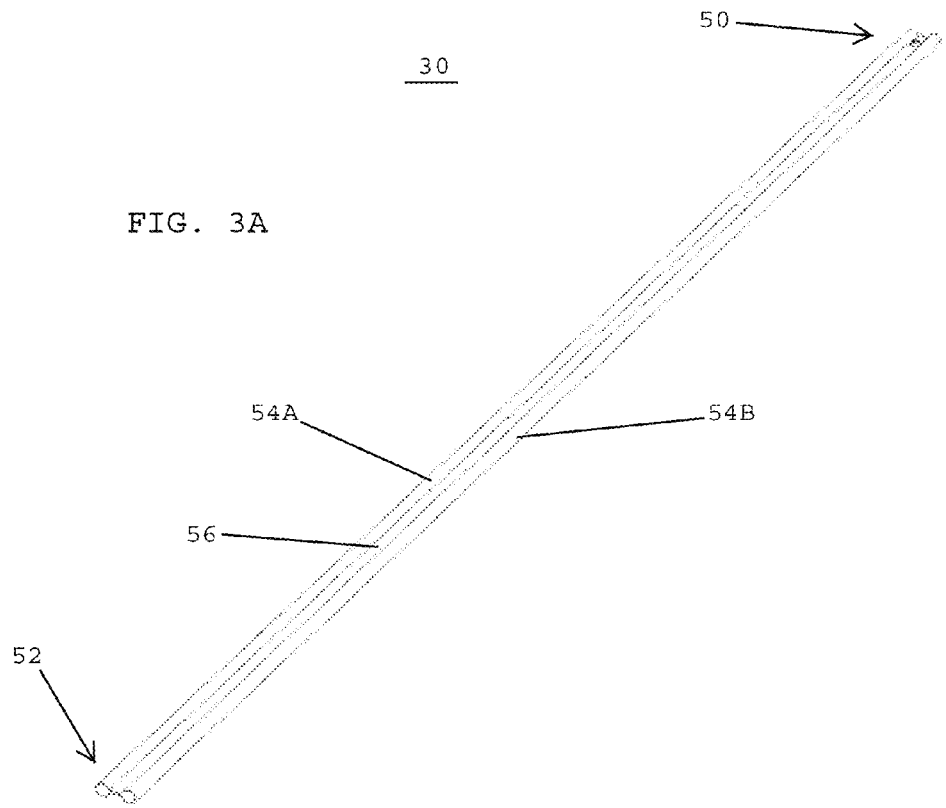
FIG. 3A shows a perspective view of the elongated core of FIG. 1, in accordance with one embodiment of the present invention.

Referring to FIG. 3A, in one embodiment, the incision guide and wound closure device preferably includes an elongated core 30 (FIG. 1) having a proximal end 50 and a distal end 52. The elongated core 30 preferably includes first and second tubular elements or tubes 54A, 54B extending between the proximal end 50 and the distal end 52 thereof. The first and second tubes 54A, 54B are preferably interconnected by an elongated central bar or slat 56 that may extend between the proximal end 50 and the distal end 52 of the elongated core 30.

Figures 3B, 3C:
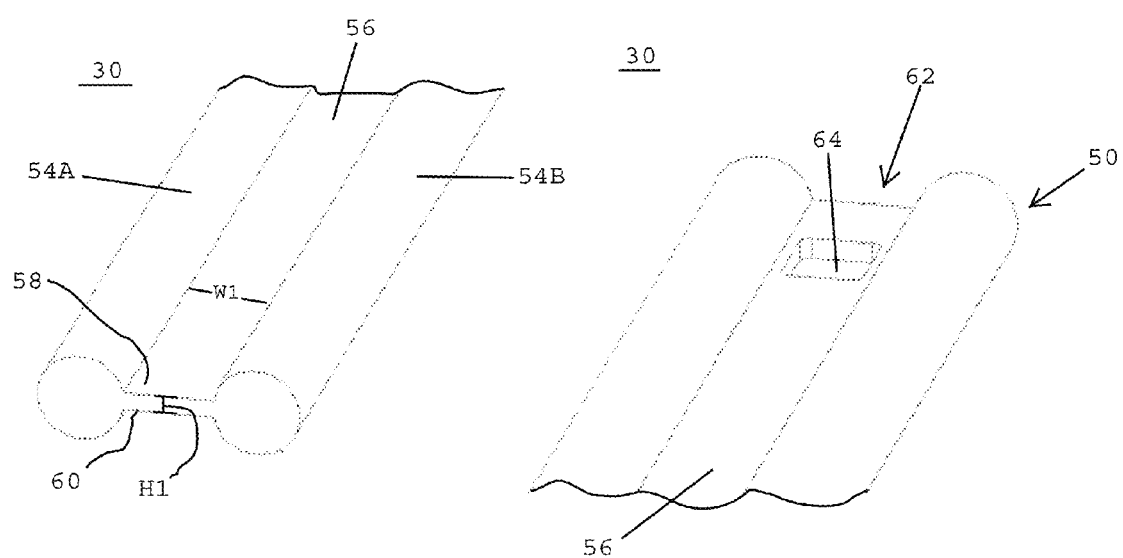
FIG. 3B shows a distal end of the elongated core of FIG. 3A.
FIG. 3C shows a proximal end of the elongated core of FIG. 3A.

Referring to FIG. 3B, in one embodiment, the elongated central bar 56 preferably extends along the length of the elongated core, between the first tube 54A and the second tube 54B for interconnecting the tubes. The central bar 56 desirable includes a top surface 58 and a bottom surface 60 defining a height $H_1$ of about 1 mm and a width $W_1$ of about 2 mm.

Referring to FIG. 3C, in one embodiment, the central bar or slat 56 preferably has a proximal end 62 that is located adjacent the proximal end 50 of the elongated core 30. The central bar 56 preferably includes an opening 64 adjacent the proximal end 62 that extends between the top surface 58 and the bottom surface 60 (FIG. 3B) thereof. As will be described in more detail below, the central opening 64 is preferably adapted to receive a section of the slideable guide 28 (FIG. 1) for attaching the slideable guide with the proximal end of the elongated core 30.

Figure 4A:
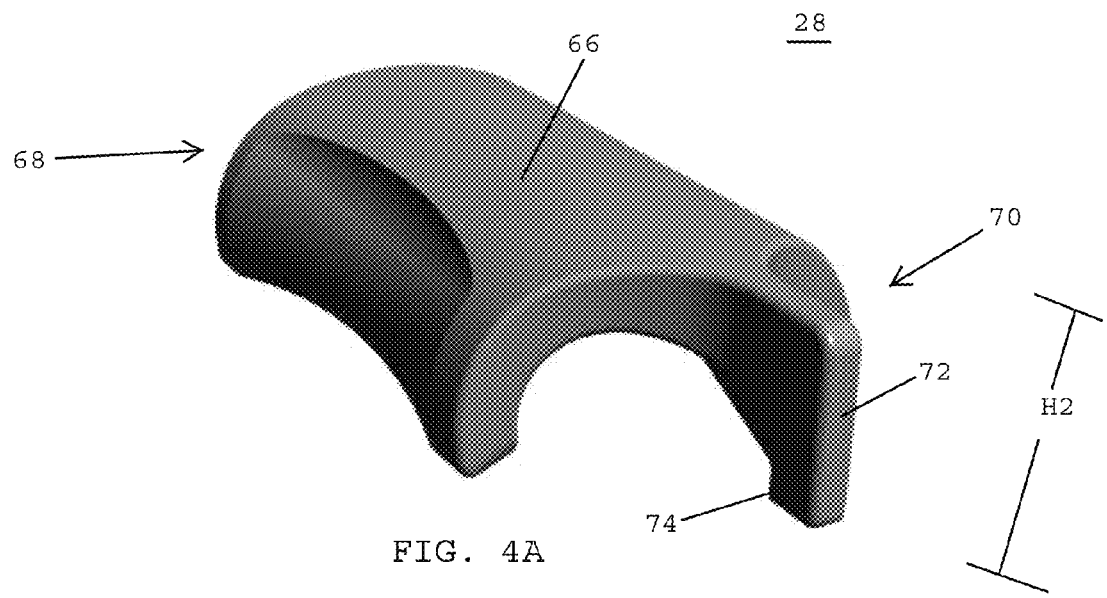
FIG. 4A shows a perspective view the slideable guide of FIG. 1.
Figure 4B:
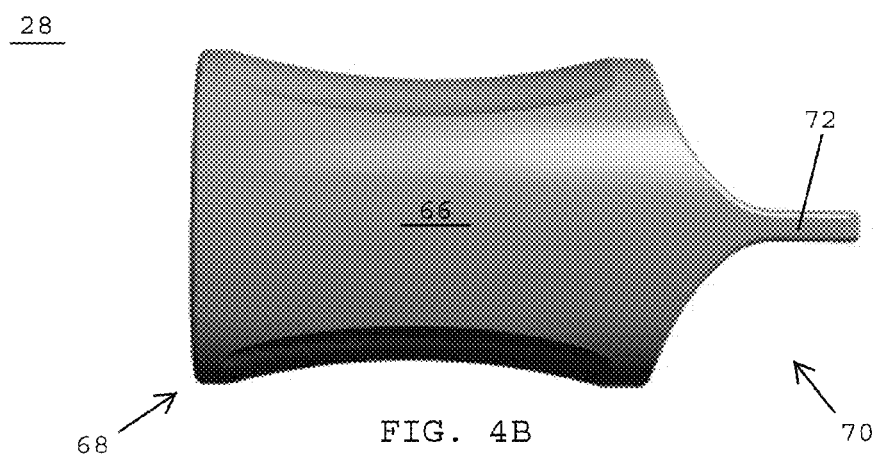
FIG. 4B shows a top plan view of the slideable guide of FIG. 4A.
Figure 4C:
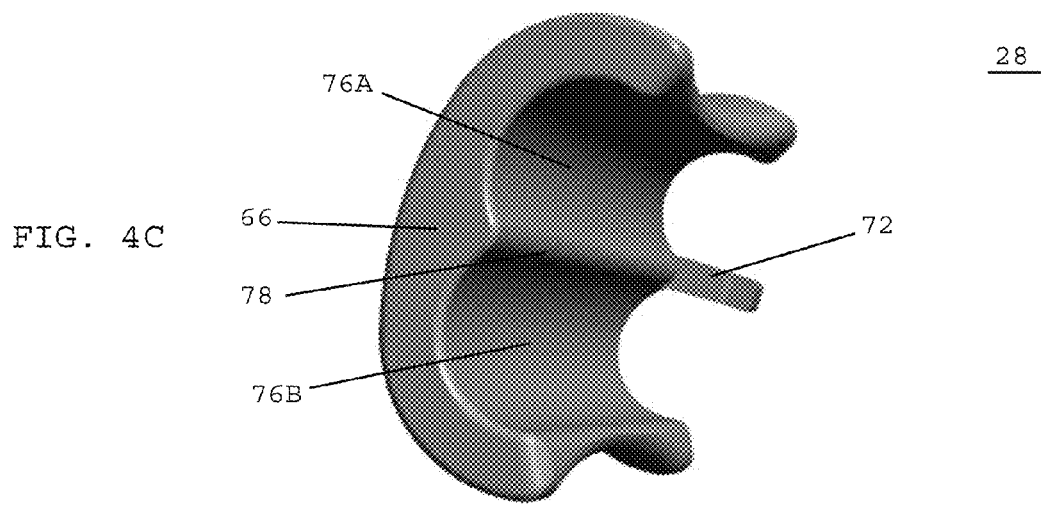
FIG. 4C shows an underside of the slideable guide of FIGS. 4A and 4B.

Referring to FIGS. 4A-4C, in one embodiment, an incision guide and wound closure device 10 preferably has a closing element 26 (FIG. 1) including a slideable guide 28 adapted to slide over the first and second incision guides 20A, 20B (FIG. 2A). The slideable guide 28 preferably includes a main body 66 having a leading or proximal end 68 and a trailing or distal end 70. The slideable guide 28 preferably includes an attachment element 72 projecting from the distal end 70 of the main body 66. The attachment element 72 desirably includes an attachment hook 74 projecting from a lower end thereof that is adapted to couple with the opening 64 adjacent the proximal end 62 of the central bar 56 of the elongated core 30 (FIG. 3C). Referring to FIG. 4A, in one embodiment, the slideable guide 28 preferably has a height $H_2$ of about 3 mm.

Referring to FIG. 4C, in one embodiment, the main body 66 of the slideable guide 28 desirably has an underside defining a first guide channel 76A and a second guide channel 76B. The first and second guide channels 76A, 76B are preferably separated from one another by a rib 78 that extends between the attachment element 72 and the proximal end 68 of the main body 66. The guide channels 76A, 76B are preferably adapted to slide over the outer surfaces of the respective first and second incision guides 20A, 20B as the slideable guide 28 moves between the distal ends 24A, 24B and the proximal ends 22A, 22B of the respective first and second incision guides 20A, 20B (FIGS. 2A and 2B).

Figure 5A:
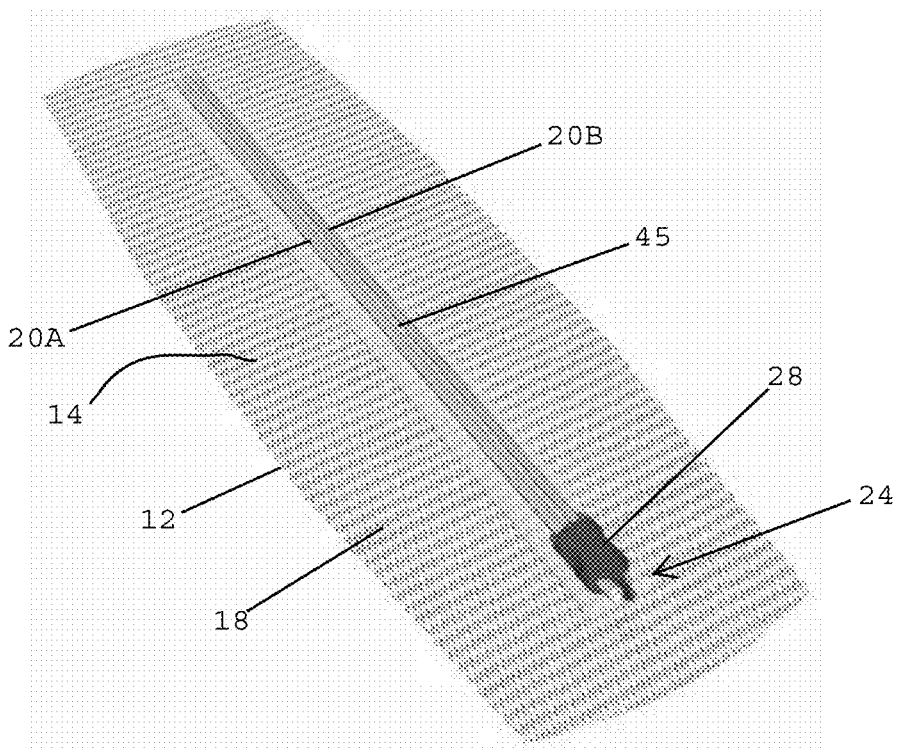
FIGS. 5A-5E show a method of making an incision and closing the incision using the incision guide and wound closure device shown in FIG. 1.

Referring to FIG. 5A, in one embodiment, during a surgical procedure the surgical mesh 12 is preferably positioned atop a patient's tissue. The first and second incision guides 20A, 20B that are attached to the top surface 14 of the mesh and are preferably held adjacent one another by the uncut, continuous mesh. The incision guides 20A, 20B preferably define an elongated gap 45 therebetween that is adapted to receive a cutting end of a cutting instrument. In one embodiment, the elongated gap 45 is preferably aligned with a desired cutting line in tissue. If the elongated gap 45 is not properly aligned, the surgical mesh may be lifted away from the skin for repositioning. In one embodiment, after the elongated gap 45 is properly aligned, a fluid tissue glue may be passed through the pores 18 (FIG. 5C-1) of the mesh 12 for more permanently attaching the mesh to the underlying tissue. The tissue glue may be cured for forming a strong bond between the mesh and the underlying skin. In one embodiment, prior to making an incision through the mesh and into the tissue, the slideable guide 28 of the closing element is preferably positioned at the distal ends 24 of the respective incision guides 20A, 20B.

Figure 5B:
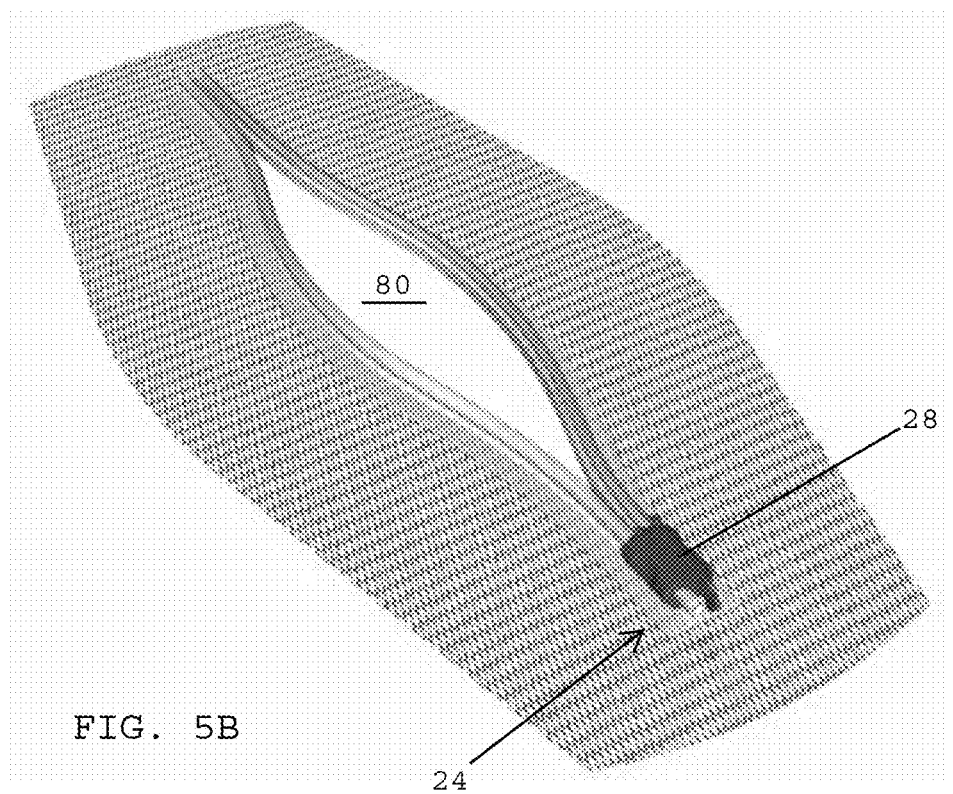
Figure 5C:
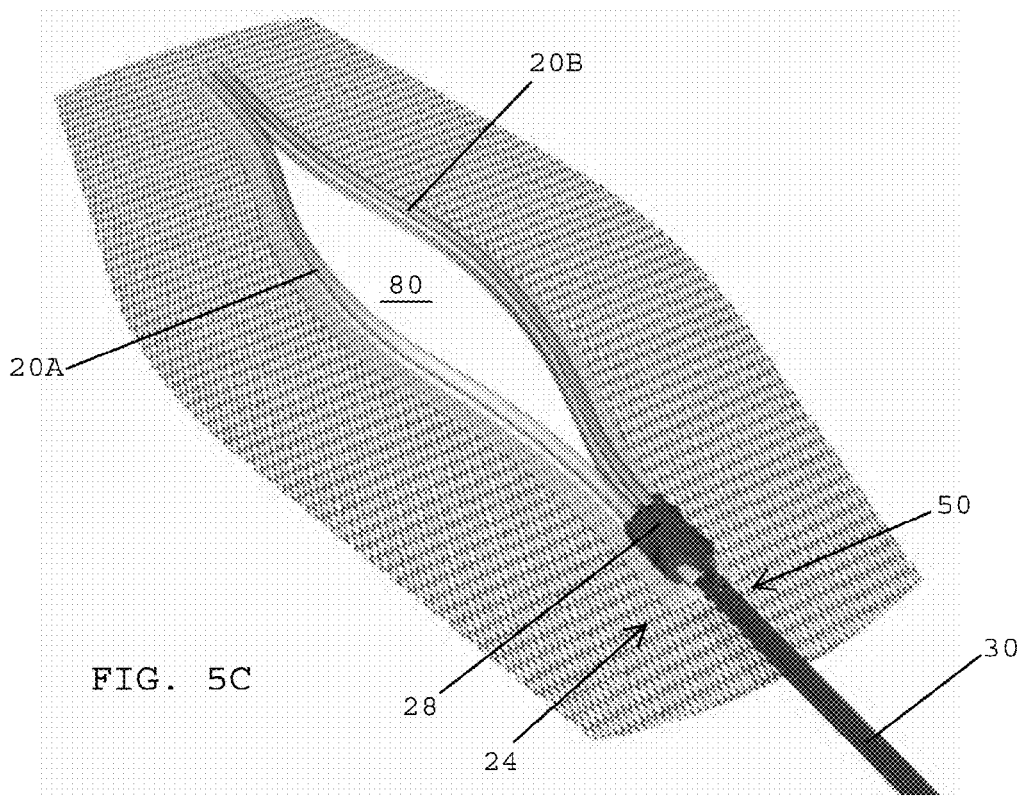
Figures 1, 5C:
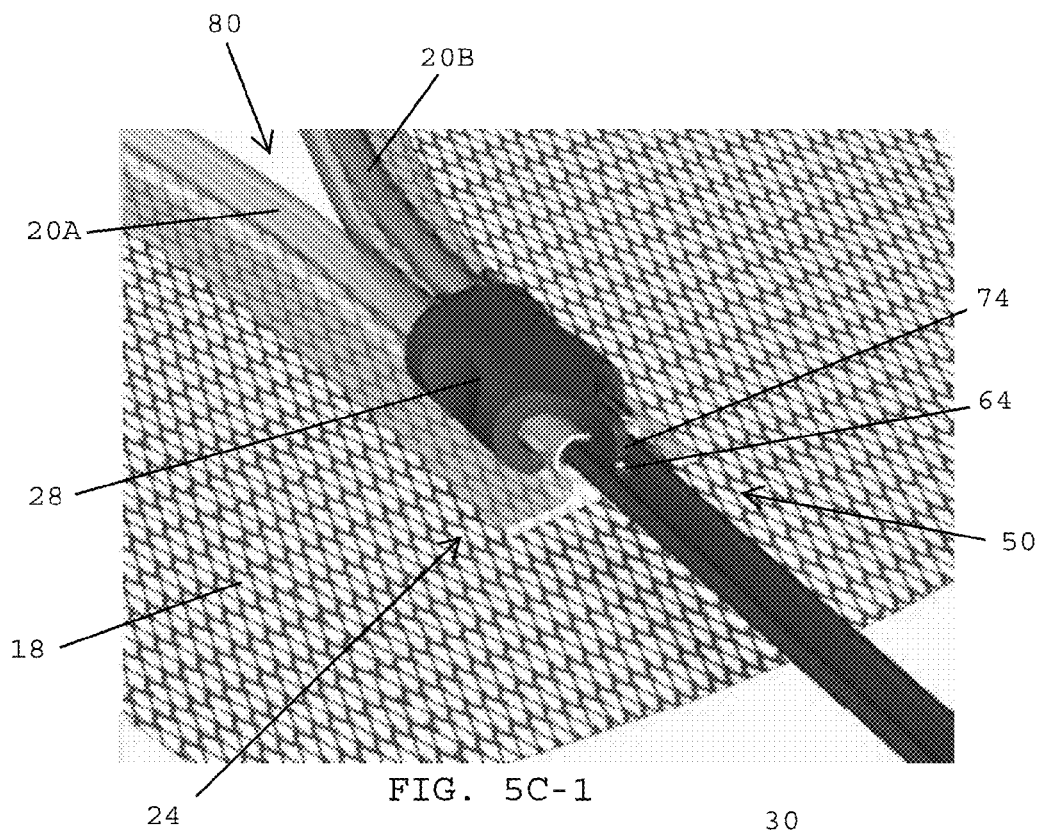

Referring to FIGS. 5A and 5B, in one embodiment, an incision 80 may be made along the elongated gap 45 located between the opposing first and second guides 20A, 20B. Medical personnel may complete the surgical procedure through the incision opening 80. Referring to FIGS. 5C and 5C-1, at the conclusion of a surgical procedure, it may be desirable to close the incision opening 80 formed in the surgical mesh 12 and located between the incision guides 20A, 20B. In one embodiment, this may be accomplished by positioning the slideable guide 28 at the distal ends 24 of the incision guides 20A, 20B and coupling the proximal end 50 of the elongated core 30 with the slideable guide 28. As shown in FIG. 5C-1, in one embodiment, the slideable guide 28 is coupled with the elongated core 30 by connecting the attachment hook 74 at the trailing end of the slideable guide with the opening 64 (FIG. 3C) at the proximal end 50 of the elongated core 30.

Figure 5D:
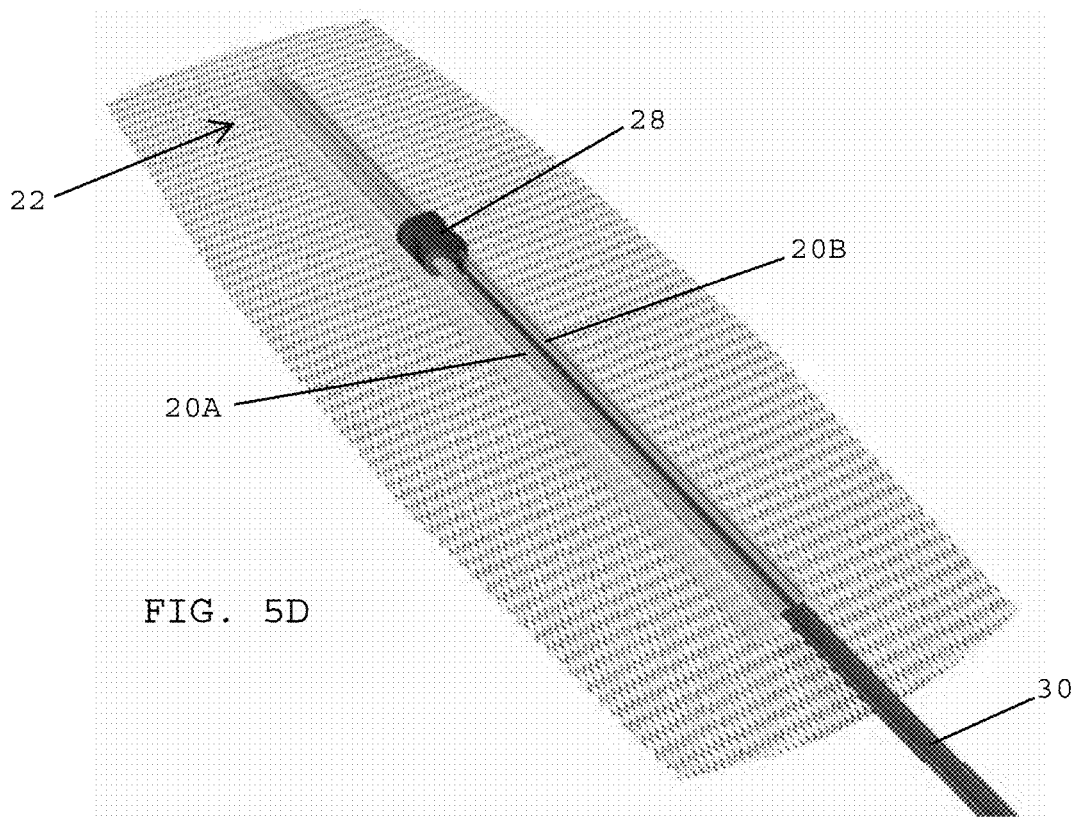
Figure 5E:
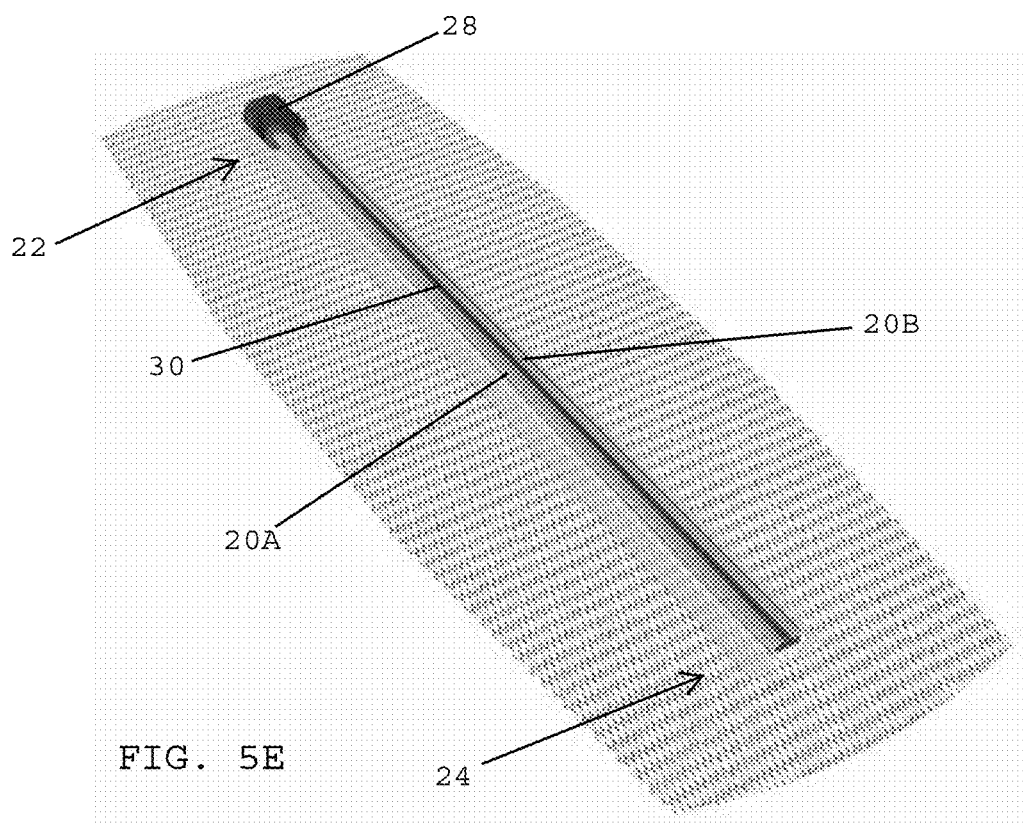
Figures 1, 5E:
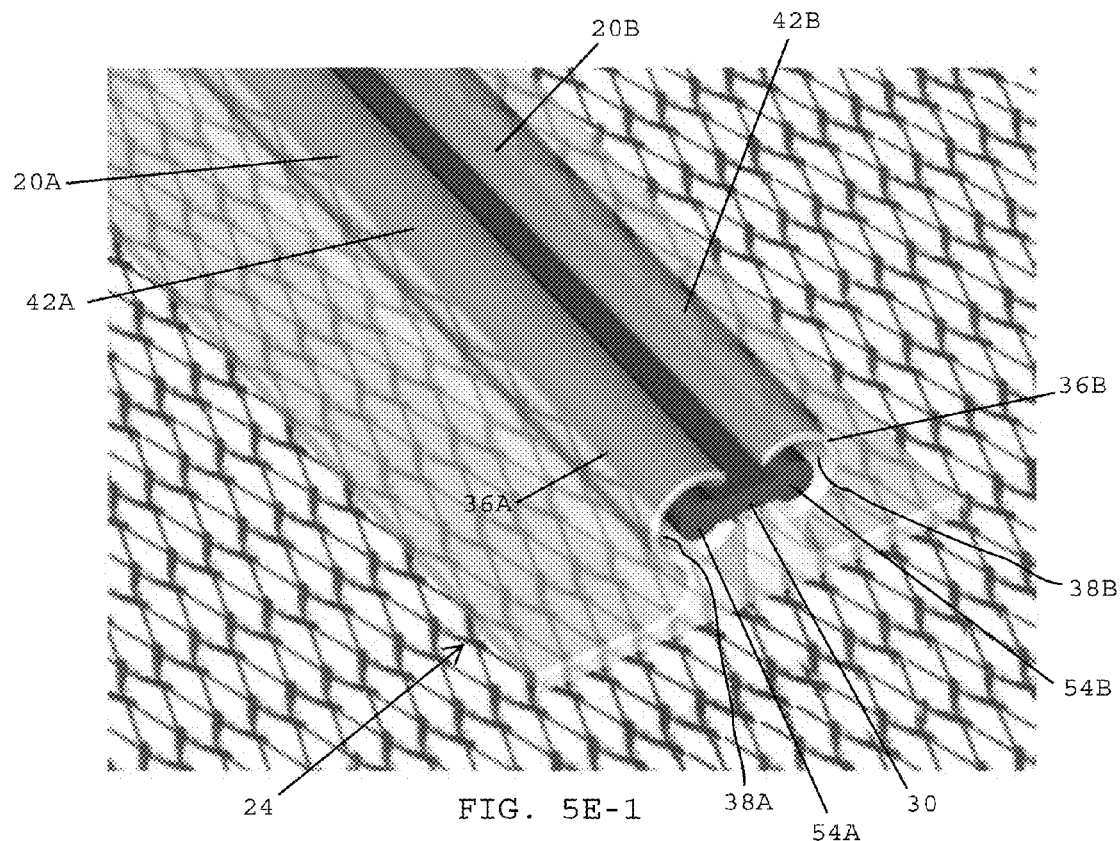

Referring to FIGS. 5C-5E, in one embodiment, the incision opening 80 and the wound may be closed by moving the slideable guide 28 and the elongated core 30 connected therewith toward the proximal ends 22 of the respective first and second incision guides 20A, 20B. As the slideable guide 28 and the elongated core 30 move toward the proximal ends 22 of the incision guides 20A, 20B, the first and second guides are desirably pulled toward one another, which, in turn, pulls the cut edges of the mesh and the underlying tissue toward one another for closing both the gap in the mesh 12 and the incision opening 80.

Referring to FIGS. 5E and 5E-1, in one embodiment, as the slideable guide 28 moves from the distal end 24 toward the proximal end 22 of the first and second guides 20A, 20B, the slideable guide 28 pulls the elongated core 30 therewith so that the first and second tubes 54A, 54B pass through the elongated channels 38A, 38B of the respective first and second incision guides 20A, 20B.

Figure 6:
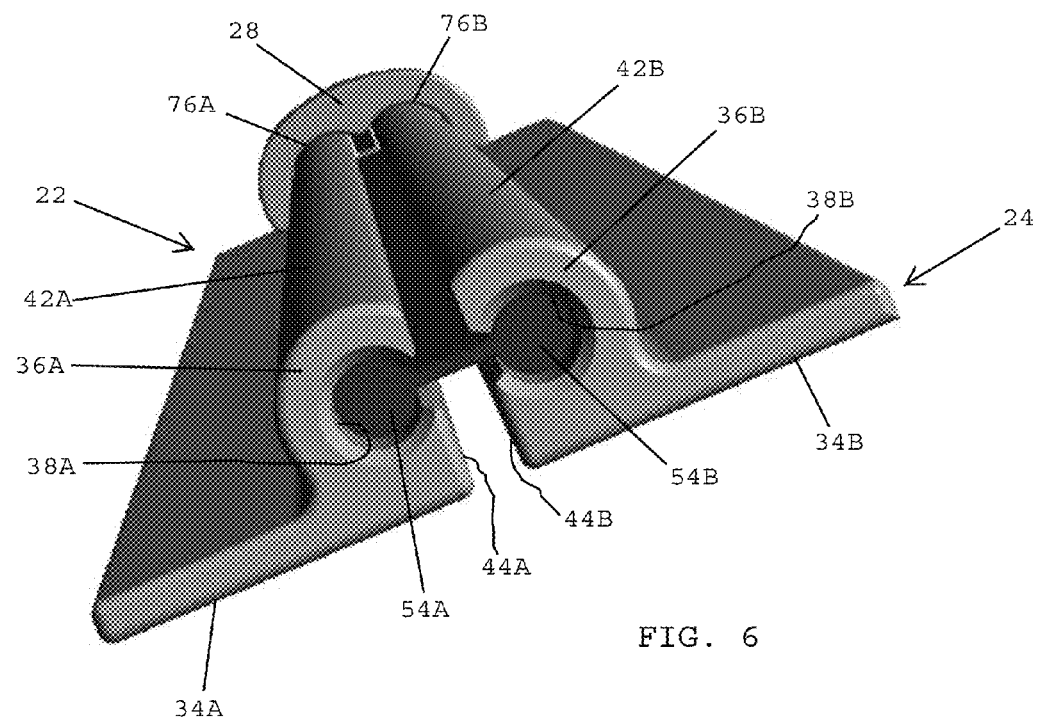
FIG. 6 shows a distal end view of the incision guides of FIG. 1 with the slideable guide of the closing element at the proximal ends of the incision guides.

Referring to FIG. 6, in one embodiment, as the slideable guide 28 slides from the distal end 24 toward the proximal end 22 of the incision guides 20A, 20B, the first and second channels 76A, 76B (FIG. 4C) located at an underside of the slideable guide 28 slide over the outer surfaces 42A, 42B of the respective first and second incision guides 20A, 20B.

FIG. 6 shows the slideable guide 28 after it has been advanced to the proximal ends 22 of the respective first and second incision guides 20A, 20B. The mesh has been removed for clarity. As the slideable guide 28 moves toward the proximal end 22, the slideable guide 28 preferably pulls the elongated core 30 through the elongated channels 38A, 38B of the first and second incision guides 20A, 20B for drawing the incision guides together to close the wound. As the slideable guide 28 is moved toward the proximal end 22 of the first and second incision guides 20A, 20B, the first and second tubes 54A, 54B pass through the elongated channels 38A, 38B for closing the device. The opposing faces 44A, 44B of the first and second incision guides 20A, 20B are pulled toward one another for closing the gap therebetween.

In one embodiment, the first tube 54A of the elongated core 30 preferably slides within the elongated channel 38A of the first curved flange 36A and the second tube 54B of the elongated core 30 preferably slides within the second elongated channel 38B of the second curved flange 36B. In one embodiment, the bottom surfaces 34A, 34B of the respective first and second bases 32A, 32B are substantially flat and are desirably adapted to be adhered to a surface of a surgical mesh (not shown). The substantially flat surfaces 34A, 34B preferably extend between the distal and proximal ends 24, 22 of the respective first and second incision guides 20A, 20B.

Referring to FIG. 7A, in one embodiment, an incision guide and wound closure device 110 may include a surgical mesh 112 having opposing first and second incision guides 120A, 120B attached to a top surface thereof. The first and second incision guides 120A, 120B may define an elongated gap 175 extending therebetween for guiding a surgical tool. In one embodiment, one or more peripheral edges of the surgical mesh 112 may have relief 125 formed therein to enable the surgical mesh 112 to be angled or curved as shown in FIG. 7B. Referring to FIG. 7B, in one embodiment, when the mesh 112 is angled or curved due to the presence of the relief 125, the elongated gap 175 between the opposing incision guides may be angulated or curved. The embodiment shown in FIG. 7B has the incision guides removed for clarity and to better define the elongated gap 175 therebetween. The opposing incision guides may be used for guiding a cutting instrument through the surgical mesh 112 and into the underlying tissue to form a surgical opening 180 that is curved or angulated. At the end of a surgical procedure, the opposing first and second incision guides 120A, 120B may be drawn together using the closing element embodiment described above. As the closing element is closed, the opposing first and second incision guides are drawn together, which, in turn, draws the opposing cut edges of the surgical mesh 112 together for closing the incision opening 180 in the underlying tissue. In one embodiment, the relief 125 may be formed by making one or more cuts or slits along the outer edges 135 of the mesh 112. In one embodiment, the relief 125 may be formed by removing sections of the mesh along the outer edges 135 of the mesh 112.

Figure 8A:
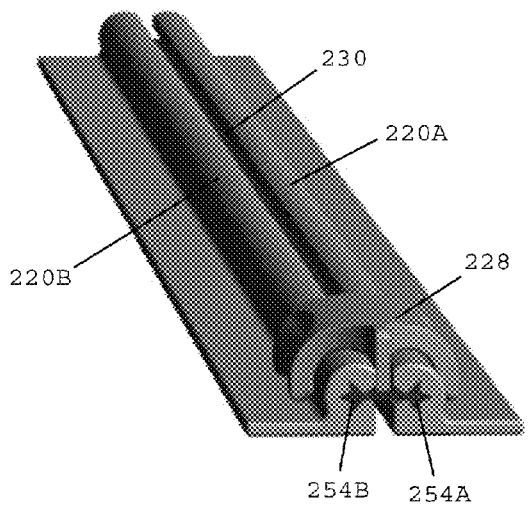
FIGS. 8A and 8B show a proximal end of an incision guide and wound closure device, in accordance with one embodiment of the present invention.
Figure 8B:
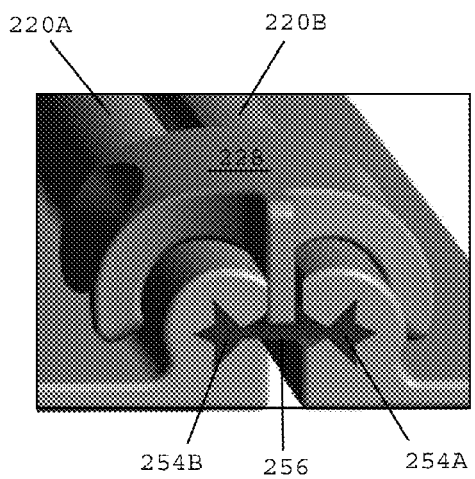

Referring to FIGS. 8A and 8B, in one embodiment, an incision guide and wound closure device 210 preferably includes first and second incision guides 220A, 220B, a slideable element 228, and an elongated core 230 coupled with the slideable element 228. In one embodiment, the incision guides 220A, 220B are preferably attached to a surgical mesh, such as the mesh 12 shown in FIG. 1, however, the surgical mesh is not shown in FIGS. 8A and 8B for purposes of clarity. The elongated core 230 preferably includes a pair of elongated elements 254A, 254B having a star-shaped cross-section, which are interconnected by an elongated slat 256. The star-shaped elongated elements 254A, 254B are adapted to be drawn through similarly configured star-shaped elongated channels extending along the lengths of the respective first and second incision guides 220A, 220B. Although the present invention is not limited by any particular theory of operation, it is believed that the star-shaped elongated elements 254A, 254B of the elongated core 230 enhance the flexibility of the incision guide and wound closure device 210, which enables the device to be more easily angled to accommodate angles incisions, bent into a curve to accommodate curved incisions.

Figure 9A:
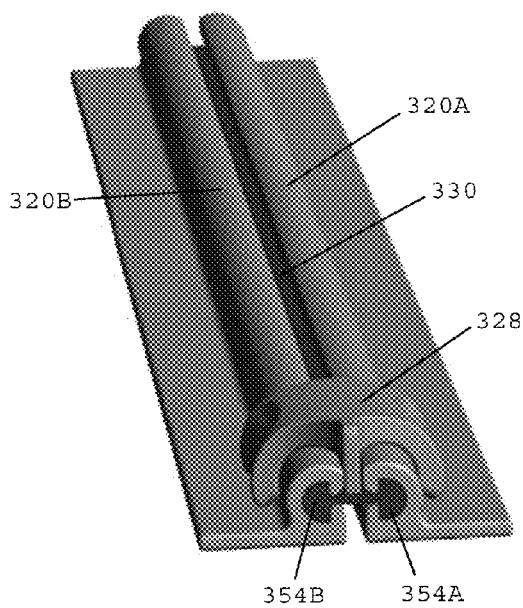
FIGS. 9A and 9B show a proximal end of an incision guide and wound closure device, in accordance with one embodiment of the present invention.
Figure 9B:
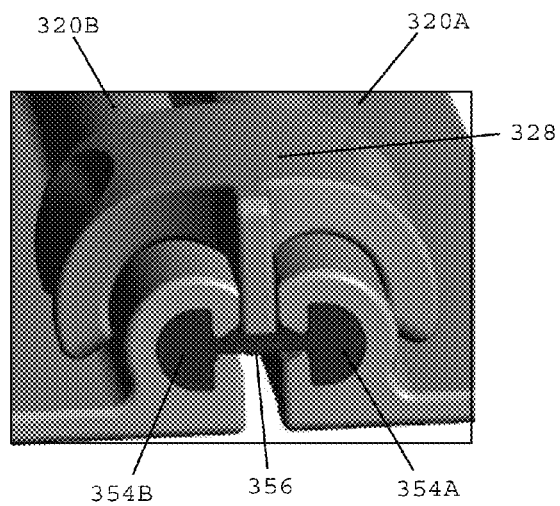

Referring to FIGS. 9A and 9B, in one embodiment, an incision guide and wound closure device 310 preferably includes first and second incision guides 320A, 320B, a slideable element 328, and an elongated core 330 coupled with the slideable element 328. In one embodiment, the incision guides 320A, 320B are preferably attached to a surgical mesh, such as the mesh 12 shown in FIG. 1, however, the surgical mesh is not shown in FIGS. 9A and 9B for purposes of clarity. The elongated core 330 preferably includes a pair of elongated elements 354A, 354B having a semi-circular cross-section, which are interconnected by an elongated slat 356. The semi-circular elongated elements 354A, 354B are adapted to be drawn through similarly shaped elongated channels extending along the lengths of the respective first and second incision guides 320A, 320B. Although the present invention is not limited by any particular theory of operation, it is believed that the semi-circular elongated elements 354A, 354B of the elongated core 330 enhance the flexibility of the incision guide and wound closure device, which enables the device to be more easily angled to accommodate angled incisions, or bent into a curve to curved incisions.

The cross-sectional shapes of the elongated cores and the elongated channels of the incision guides shown in FIGS. 8A-8B and 9A-9B are merely exemplary in nature and may be modified to provide a device that is flexible for accommodating a wide variety of curved and angled incisions. In one embodiment, the incision guide and wound closure device may be used on an incision having two or more distinct curves. In one embodiment, the incision guide and wound closure device may be used on an incision having two or more distinct angles. Other cross-sectional shapes may be used for the elongated cores and the elongated channels of the incision guides including cruciform shapes, I-beam shapes, etc.

Figure 10A:
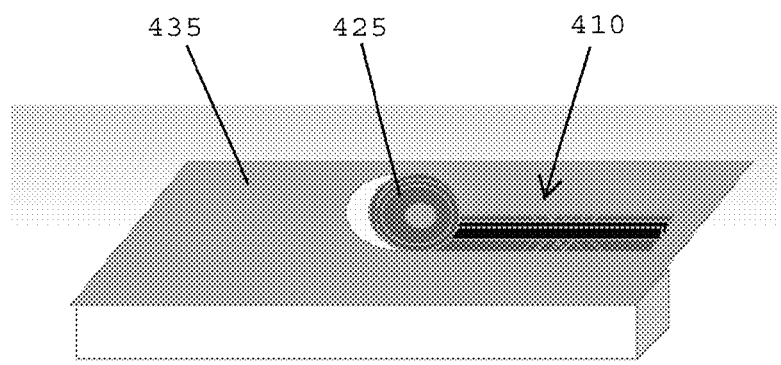
FIGS. 10A and 10B show a length-adjustable incision guide and wound closure device, in accordance with one embodiment of the present invention.
Figure 10B:
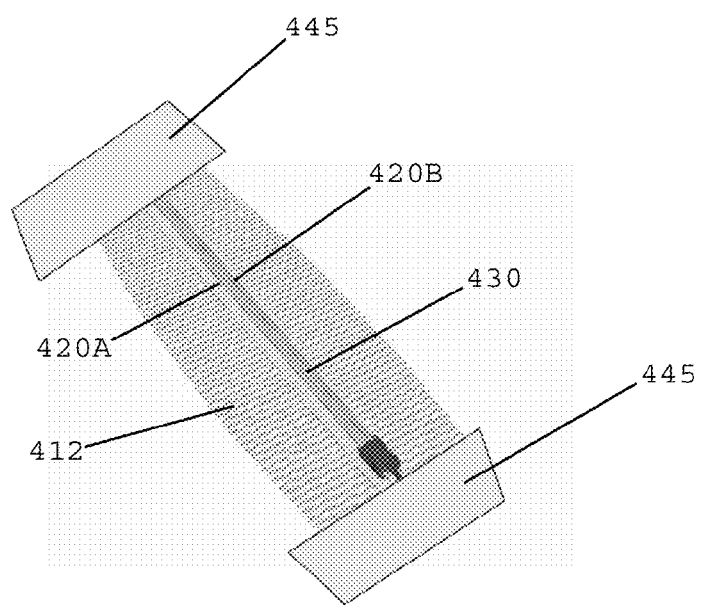

Referring to FIGS. 10A and 10B, in one embodiment, an incision guide and wound closure device 410 may be wound into a roll for shipment and storage. Referring to FIG. 10A, in one embodiment, after a surgeon determines a length of an incision required for a surgical procedure, the surgeon may unwind the roll and cut a section of the roll to provide an incision guide and wound closure device having a desired length. In one embodiment, medical personnel may unwind the roll 425 onto a flat support surface 435. Referring to FIG. 10B, in one embodiment, when the mesh 412 has been unwound, a cutting instrument 445 may be used for cutting the surgical mesh 412, the first and second incision guides 420A, 420B, and the elongated core 430 to the desired length. In one embodiment, the mesh, the incision guides, and the elongated core are cut at the same time and to the same length. In one embodiment, a plurality of incision guide and wound closure devices having different sizes and/or lengths may be provided to medical personnel. In one embodiment, medical personnel may select one of the devices having the proper size, length and/or width that satisfies the particular surgical needs of a patient. In one embodiment, a plurality of incision guide and wound closure devices having different sizes, lengths and/or widths may be provided, and a surgeon may cut or trim a selected one of the plurality of devices to suit surgical requirements.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An incision guide and wound closure device comprising:
    a surgical mesh having a plurality of pores, a top surface and a bottom surface;
    a first incision guide affixed to said top surface of said surgical mesh, said first incision guide having a first end, a second end, and a first alignment surface extending between said first and second ends thereof;
    a second incision guide affixed to said top surface of said surgical mesh adjacent said first incision guide, said second incision guide having a first end, a second end, and a second alignment surface extending between said first and second ends thereof that opposes said first alignment surface of said first incision guide;
    a closing element engageable with said first and second incision guides, said closing element being moveable between said first and second ends of said respective first and second incision guides for drawing said first and second alignment surfaces toward one another;
    said closing element including an elongated core having an elongated slat, the elongated slat having a top surface and a bottom surface that opposes said top surface of said surgical mesh, said elongated slat having a proximal end, a distal end, and an opening spaced from said proximal end of said elongated slat that extends from said top surface to said bottom surface of said elongated slat, said closing element including a slideable element having an attachment flange engageable with said opening of said elongated slat for connecting said slideable element and said elongated core together, wherein said connected slideable element overlies said top surface of said elongated slat and is slideable over said first and second incision guides for pulling said elongated core through said first and second incision guides so as to draw said first and second incision guides together;
    a first adhesive covering said bottom surface of said surgical mesh for forming a relatively weaker bond between said surgical mesh and a skin surface for facilitating initial placement and alignment of said surgical mesh atop said skin surface, wherein after said surgical mesh has been bonded to said skin surface using said first adhesive, said first adhesive enables said surgical mesh to be peeled away from and repositioned atop said skin surface for aligning said surgical mesh atop said skin surface;
    a second adhesive passable through said plurality of pores of said surgical mesh for forming a relatively stronger bond between said surgical mesh and said skin surface than is formed by said first adhesive, wherein said second adhesive is utilized only after said surgical mesh is properly aligned atop said skin surface.

2. The device as claimed in claim 1, wherein said first and second alignment surfaces define an elongated gap therebetween adapted to receive a cutting instrument for cutting through said surgical mesh so as to form an incision through said surgical mesh that extends between said first and second incision guides.

3. The device as claimed in claim 2, wherein said incision through said surgical mesh is closed as said slideable element of said closing element moves from said first ends to said second ends of said respective first and second incision guides.

4. The device as claimed in claim 2, wherein said first and second alignment surfaces on said adjacent incision guides are adapted to engage said cutting instrument for properly aligning said cutting instrument relative to said top surface of said surgical mesh.

5. The device as claimed in claim 1, wherein said surgical mesh comprises said plurality of pores extending from said top surface to said bottom surface of said surgical mesh.

6. The device as claimed in claim 1, wherein said second adhesive is clear or translucent for enabling visibility of said incision and said skin surrounding said incision through said pores of said surgical mesh.

7. The device as claimed in claim 1, wherein said first incision guide includes a first base secured to said top surface of said surgical mesh and a first flange projecting upwardly from said first base, and wherein said second incision guide includes a second base secured to said top surface of said surgical mesh and a second flange projecting upwardly from said second base.

8. The device as claimed in claim 7, wherein said slideable element of said closing element is adapted to slide over said first and second flanges for drawing said first and second incision guides toward one another for closing said incision opening.

9. The device as claimed in claim 8, wherein said first flange has a first outer surface and a first inner surface defining a first elongated channel that extends along a length of said first flange, and said second flange has a second outer surface and a second inner surface defining a second elongated channel that extends along a length of said second flange.

10. The device as claimed in claim 9, wherein said elongated core comprises:
a first tubular element adapted to advance within said first elongated channel;
a second tubular element adapted to advance within said second elongated channel;
said elongated slat interconnecting said first and second tubular elements.

11. The device as claimed in claim 10, wherein said opening in said elongated slat is a central opening that is spaced from said proximal end of said elongated slat, said central opening being located between said proximal and distal ends of said elongated slat, and said central opening being spaced from lateral sides of said elongated slat.

12. The device as claimed in claim 11, wherein said first elongated channel has a first linear opening and said first tubular element has a diameter that is larger than said first linear opening and said second elongated channel has a second linear opening and said second tubular element has a diameter that is larger than said second linear opening, and wherein said first and second linear openings oppose one another so that said elongated slat is extendable through said first and second linear openings for interconnecting said first and second tubular elements.

13. An incision guide and wound closure device comprising:
a surgical mesh having a top surface and a bottom surface;
a first incision guide affixed to said top surface of said surgical mesh, said first incision guide having a first end, a second end, and a first alignment surface extending between said first and second ends thereof;
a second incision guide affixed to said top surface of said surgical mesh adjacent said first incision guide, said second incision guide having a first end, a second end, and a second alignment surface extending between said first and second ends thereof that opposes said first alignment surface of said first incision guide;
a closing element engageable with said first and second incision guides, said closing element being moveable between said first and second ends of said respective first and second incision guides for drawing said first and second alignment surfaces toward one another, wherein said first and second incision guides are flexible;
said closing element including an elongated core having an elongated slat, the elongated slot having a top surface and a bottom surface that opposes said top surface of said surgical mesh, said elongated slat having a proximal end, a distal end, and an opening spaced from said proximal end of said elongated slat that extends from said top surface to said bottom surface of said elongated slat, said closing element including a slideable element having an attachment flange engageable with said opening of said elongated slat for connecting said slideable element and said elongated core together, wherein said connected slideable element overlies said top surface of said elongated slat and is slideable over said first and second incision guides for pulling said elongated core through said first and second incision guides so as to draw said first and second incision guides together;
said device further comprising a first cut formed in a first outer edge of said surgical mesh and extending toward said first incision guide and a second cut formed in a second outer edge of said surgical mesh and extending toward said second incision guide for flexing said first and second incision guides to form a non-linear gap between said first and second incision guides, wherein said first and second outer edges are located on opposite sides of said incision guides.

14. The device as claimed in claim 13, further comprising:
a plurality of first cuts formed in said first outer edge of said surgical mesh and extending toward said first incision guide; and
a plurality of second cuts formed in said second outer edge of said surgical mesh and extending toward said second incision guide, wherein said plurality of first cuts and said plurality of second cuts are located on opposite sides of said incision guides.

15. An incision guide and wound closure device comprising:
a surgical mesh having pores;
first and second incision guides projecting above a top surface of said surgical mesh, said first and second incision guides being located adjacent one another and having opposing alignment surfaces adapted to guide a cutting instrument for forming an incision through said surgical mesh;
a closing element engageable with said first and second incision guides, said closing element being moveable along said incision guides for drawing said first and second alignment surfaces toward one another for closing said incision in said surgical mesh;
said closing element including an elongated core having an elongated slat, the elongated slot having a top surface and a bottom surface that opposes said top surface of said surgical mesh, said elongated slat having a proximal end, a distal end, and an opening spaced from said proximal end of said elongated slat that extends from said top surface to said bottom surface of said elongated slat, said closing element including a slideable element having an attachment flange engageable with said opening of said elongated slat for connecting said slideable element and said elongated core together, wherein said connected slideable element overlies said top surface of said elongated slat and is slideable over said first and second incision guides for pulling said elongated core through said first and second incision guides so as to draw said first and second incision guides together;

a first adhesive covering said bottom surface of said surgical mesh for forming a relatively weaker bond between said surgical mesh and a skin surface for facilitating initial placement and alignment of said surgical mesh atop said skin surface, wherein after said surgical mesh has been bonded to said skin surface using said first adhesive, said first adhesive enables said surgical mesh to be peeled away from and repositioned atop said skin surface for aligning said surgical mesh atop said skin surface;

a second adhesive passable through said pores of said surgical mesh for forming a relatively stronger bond between said surgical mesh and said skin surface than is formed by said first adhesive, wherein said second adhesive is utilized only after said surgical mesh is properly aligned atop said skin surface.

16. The device as claimed in claim 15, wherein said opening in said elongated slat is a central opening that is located between said proximal and distal ends of said elongated slat, and wherein said device further comprises a clear or translucent adhesive passable through said pores for adhering said surgical mesh to a skin surface.

17. A method of making and closing an incision comprising:

providing an incision guide and wound closure device including a mesh having pores, a top surface and a bottom surface, first and second incision guides affixed to said top surface of said mesh, and a closing element engageable with said first and second incision guides;

said closing element including an elongated core having an elongated slat, the elongated slot having a top surface and a bottom surface that opposes said top surface of said mesh, said elongated slat having a proximal end, a distal end, and an opening spaced from said proximal end of said elongated slat that extends from said top surface to said bottom surface of said elongated slat, said closing element including a slideable element having an attachment flange engageable with said opening of said elongated slat for connecting said slideable element and said elongated core together, wherein said connected slideable element overlies said top surface of said elongated slat and is slideable over said first and second incision guides for pulling said elongated core through said first and second incision guides so as to draw said first and second incision guides together;

providing a first adhesive over said bottom surface of said mesh;

positioning said bottom surface of said mesh atop tissue so that said first adhesive forms a relatively weak bond between said mesh and said tissue;

after said mesh is properly aligned atop said tissue, applying a second adhesive through said pores of said mesh for adhering said mesh to said tissue, wherein said second adhesive forms a stronger bond between said mesh and said tissue than is formed by said first adhesive;

advancing a cutting instrument between said first and second incision guides for making an incision through said mesh and into said tissue;

performing a surgical procedure within said incision;

connecting said slideable element with said elongated slat so that said slideable element overlies said top surface of said elongated slat;

sliding said connected slideable element over said first and second incision guides for pulling said elongated core through said first and second incision guides and drawing said first and second incision guides toward one another for closing said incision.

18. The method as claimed in claim 17, further comprising peeling said mesh away from said tissue for breaking said bond between said mesh and said tissue and then repositioning said mesh atop said tissue to properly align said mesh atop said tissue.

* * * * *